(12) United States Patent
Ebbitt

(10) Patent No.: US 12,171,421 B2
(45) Date of Patent: *Dec. 24, 2024

(54) JOINT GAP BALANCING LEVER AND METHODS OF USE THEREOF

(71) Applicant: MAKO Surgical Corp., Weston, FL (US)

(72) Inventor: Peter Ebbitt, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/135,491

(22) Filed: Apr. 17, 2023

(65) Prior Publication Data

US 2023/0248348 A1  Aug. 10, 2023

Related U.S. Application Data

(63) Continuation of application No. 17/874,541, filed on Jul. 27, 2022, now Pat. No. 11,653,907, which is a continuation of application No. 16/837,543, filed on Apr. 1, 2020, now Pat. No. 11,432,811.

(60) Provisional application No. 62/845,577, filed on May 9, 2019.

(51) Int. Cl.
*A61B 17/02* (2006.01)
*A61B 34/20* (2016.01)
*A61B 90/00* (2016.01)

(52) U.S. Cl.
CPC ............ *A61B 17/025* (2013.01); *A61B 34/20* (2016.02); *A61B 2034/2051* (2016.02); *A61B 2034/2055* (2016.02); *A61B 2034/2059* (2016.02); *A61B 2090/036* (2016.02); *A61B 2090/064* (2016.02); *A61B 90/39* (2016.02)

(58) Field of Classification Search
CPC .................. A61B 17/025; A61B 34/20; A61B 2034/2051; A61B 2034/2059; A61B 2090/036; A61B 2090/064; A61B 90/39
See application file for complete search history.

(56) References Cited

U.S. PATENT DOCUMENTS

| 4,995,875 | A  | 2/1991  | Coes |
| 5,470,354 | A  | 11/1995 | Hershberger et al. |
| 5,649,929 | A  | 7/1997  | Callaway |
| 6,558,392 | B1 | 5/2003  | Martini |

(Continued)

FOREIGN PATENT DOCUMENTS

| DE | 20 2010 000 341 U1 | 5/2010 |
| EP | 2 011 442 A1 | 1/2009 |
| GB | 2 455 182 | 6/2009 |

OTHER PUBLICATIONS

U.S. Appl. No. 62/817,355, filed Mar. 12, 2019, Mako Surgical Corp.

(Continued)

*Primary Examiner* — Kevin T Truong
*Assistant Examiner* — Diana Jones
(74) *Attorney, Agent, or Firm* — FOLEY & LARDNER LLP

(57) ABSTRACT

A joint distraction lever includes a lever body, a projection coupled to the lever body such that the projection is movable relative to the lever body, and a force sensor positioned between the lever body and the projection and configured to measure a force of the projection on the lever body.

20 Claims, 9 Drawing Sheets

(56) References Cited

U.S. PATENT DOCUMENTS

| | | |
|---|---|---|
| 6,859,661 B2 | 2/2005 | Tuke |
| 7,412,897 B2 | 8/2008 | Crottet et al. |
| 7,442,196 B2 | 10/2008 | Fisher et al. |
| 7,615,055 B2 | 11/2009 | DiSilvestro |
| 7,837,691 B2 | 11/2010 | Cordes et al. |
| 8,010,180 B2 | 8/2011 | Quaid et al. |
| 8,118,815 B2 | 2/2012 | Van Der Walt |
| 8,197,489 B2 | 6/2012 | Chessar et al. |
| 8,211,041 B2 | 7/2012 | Fisher et al. |
| 8,323,290 B2 | 12/2012 | Metzger et al. |
| 8,337,508 B2 | 12/2012 | Lavallee et al. |
| 8,491,589 B2 | 7/2013 | Fisher et al. |
| 8,506,571 B2 | 8/2013 | Chana et al. |
| 8,516,907 B2 | 8/2013 | Stein et al. |
| 8,998,910 B2 | 4/2015 | Borja et al. |
| 9,351,850 B2 | 5/2016 | Fischer et al. |
| 9,439,656 B2 | 9/2016 | Chana et al. |
| 9,538,953 B2 | 1/2017 | Sherman et al. |
| 9,539,116 B2 | 1/2017 | Claypool et al. |
| 9,554,745 B2 | 1/2017 | Nguyen et al. |
| 9,572,588 B2 | 2/2017 | Fisher et al. |
| 9,642,571 B2 | 5/2017 | Mcintosh et al. |
| 2005/0038442 A1 | 2/2005 | Freeman |
| 2007/0066917 A1 | 3/2007 | Hodorek et al. |
| 2007/0244488 A1 | 10/2007 | Metzger et al. |
| 2009/0018544 A1 | 1/2009 | Heavener |
| 2009/0270869 A1 | 10/2009 | Colquhoun et al. |
| 2010/0198275 A1 | 8/2010 | Chana et al. |
| 2010/0217156 A1 | 8/2010 | Fisher et al. |
| 2010/0249658 A1 | 9/2010 | Sherman et al. |
| 2010/0250571 A1 | 9/2010 | Pierce et al. |
| 2010/0326210 A1 | 12/2010 | Stein et al. |
| 2010/0331737 A1 | 12/2010 | Stein et al. |
| 2011/0319755 A1 | 12/2011 | Stein et al. |
| 2012/0172762 A1 | 7/2012 | Boyer et al. |
| 2012/0232429 A1 | 9/2012 | Fischer et al. |
| 2012/0330368 A1 | 12/2012 | Dunn |
| 2013/0023795 A1 | 1/2013 | Stein et al. |
| 2013/0079669 A1 | 3/2013 | Stein et al. |
| 2013/0079670 A1 | 3/2013 | Stein et al. |
| 2013/0079674 A1 | 3/2013 | Stein et al. |
| 2013/0079675 A1 | 3/2013 | Stein et al. |
| 2013/0079884 A1 | 3/2013 | Stein et al. |
| 2013/0102929 A1 | 4/2013 | Haight et al. |
| 2013/0103038 A1 | 4/2013 | Fischer et al. |
| 2013/0226036 A1 | 8/2013 | Stein et al. |
| 2014/0012270 A1 | 1/2014 | Fossez et al. |
| 2015/0342588 A1* | 12/2015 | Bechtold ............ A61B 17/1675 606/90 |
| 2016/0278754 A1* | 9/2016 | Todorov .................. A61F 2/389 |
| 2016/0346044 A1 | 12/2016 | Brown et al. |
| 2017/0156736 A1 | 6/2017 | Claypool et al. |
| 2017/0245872 A1 | 8/2017 | Rock et al. |
| 2017/0360512 A1 | 12/2017 | Couture et al. |
| 2018/0049895 A1 | 2/2018 | Haight et al. |
| 2018/0085134 A1 | 3/2018 | Uthgenannt |
| 2018/0098774 A1 | 4/2018 | Bonutti |
| 2019/0388078 A1 | 12/2019 | Otto et al. |

OTHER PUBLICATIONS

U.S. Appl. No. 62/894,130, filed Aug. 30, 2019, Mako Surgical Corp.

U.S. Appl. No. 62/905,037, filed Sep. 24, 2019, Mako Surgical Corp.

International Search Report and Written Opinion for International Application No. PCT/US2015/032973, mailed Sep. 24, 2015, 14 pages.

* cited by examiner

JOINT GAP BALANCING LEVER AND METHODS OF USE THEREOF

CROSS-REFERENCE TO RELATED APPLICATIONS

This application is a continuation of U.S. patent application Ser. No. 17/874,541, filed Jul. 27, 2022, which is a continuation of U.S. patent application Ser. No. 16/837,543, filed Apr. 1, 2020, now U.S. Pat. No. 11,432,811, which claims the benefit of and priority to U.S. Provisional Application No. 62/845,577, filed May 9, 2019, the entire disclosures of which are incorporated by reference herein in their entireties.

BACKGROUND

The present disclosure relates generally to surgical tools for use during planning and preparation of a joint replacement procedure, and more particularly to a joint gap balancing lever for use during joint distraction.

Over time, as a result of disease, injury, or longevity of use, bones of a joint may degenerate, resulting in pain and diminished functionality. To reduce pain and restore functionality, a joint replacement procedure may be necessary. Examples of such procedures may be total or partial knee arthroplasty, total hip arthroplasty, or knee or hip resurfacing. In these procedures, portions of a patient's joint are replaced with artificial components. Particularly, a surgeon uses a surgical cutting tool to remove portions of bone to prepare the bone to receive a prosthetic device. Prior to resection of the bone, the surgeon plans bone preparation specific to the patient's anatomy, size, current state of the target joint, and several other factors in order to determine the portions of the bone that will be removed and replaced by one or more prosthetic components, as well as to determine proper positioning of the one or more prosthetic components.

One step of surgical planning for a partial knee resurfacing procedure involves a knee joint distraction, that is, forced separation of the distal femur from the proximal tibia. For partial knee resurfacing, this is intended to correct knee joint deformity and cause proper re-tensioning of the ligaments of the knee to determine a desired, post-procedure joint construction. In one exemplary method, prior to resection and prior to a creating a final implant plan, the knee joint deformity is corrected at multiple flexion positions or flexion angles by distracting the joint. An instantaneous six degree-of-freedom (DOF) position (i.e. the pose) of the femur with respect to the six DOF position of the tibia is captured at each of the multiple flexion positions. Resection, implant positioning, and implant characteristics are then planned based on the gathered poses so as to maintain this preferred soft tissue balance. Once the bone is resected at this desired plan and the trials and/or implants are positioned in the joint, the desired joint balance should be achieved.

SUMMARY

One implementation of the present disclosure is a joint distraction device. The joint distraction device includes a lever body and a foot extending from a bottom surface of the lever body. The foot is coupled to the lever body via a hinge such that the lever body is rotatable relative to the foot. A first plate and a second plate extend from a distal portion of the lever body, and the first plate and the second plate are separated by a gap. Each of the first plate and the second plate include a stopper extending upwards from a top surface of the first plate and the second plate. A force measurement device is coupled to the bottom surface of the lever body and configured to measure a distraction force applied by the lever body at the foot during a joint distraction procedure in which a torque is applied at a proximal portion of the lever body.

Another implementation of the present disclosure is a method for performing joint distraction. The method includes moving a joint comprising a first bone and a second bone into a first flexion position and inserting a joint distraction device into a space between the first bone and the second bone. The joint distraction device includes a lever body and a foot extending from a bottom surface of the lever body. The foot is configured to contact the front surface of the second bone. The joint distraction device also includes a first plate and a second plate extending from a distal portion of the lever body, such that the first plate and the second plate are separated by a gap. Each of the first plate and the second plate include a stopper extending upwards from a top surface of the first plate and the second plate. The force measurement device is configured to measure a distraction force applied at the foot during a distraction procedure for a joint during which a force is applied at a proximal portion of the lever body. The method also includes applying the force to the proximal portion of the lever body to cause a torque on the joint distraction device, receiving feedback from the force measurement device related to the amount of distraction force being applied to the second bone at the foot, receiving feedback from a tracking system related to a position of the first bone and the second bone, and using the combination of the feedback from the force measurement device and the feedback from the tracking system to determine an optimal gap distance between the first and second bone.

This summary is illustrative only and is not intended to be in any way limiting. Other aspects, features, and advantages of the devices or processes described herein will become apparent in the detailed description set forth herein, taken in conjunction with the accompanying figures, wherein like reference numerals refer to like elements.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Figure 1:
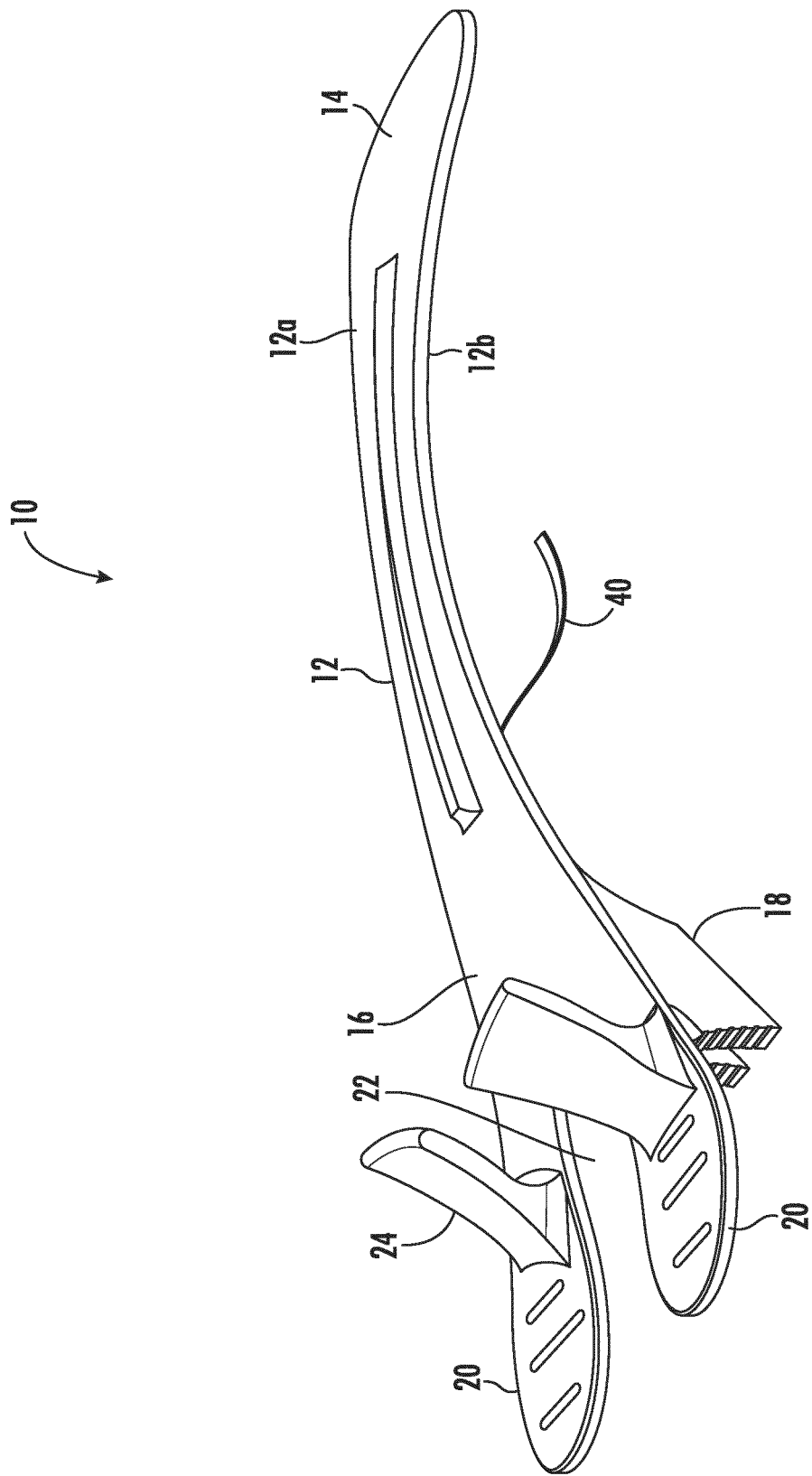
FIG. 1 is a perspective view of a joint gap balancing lever, according to an exemplary embodiment.
Figure 2:
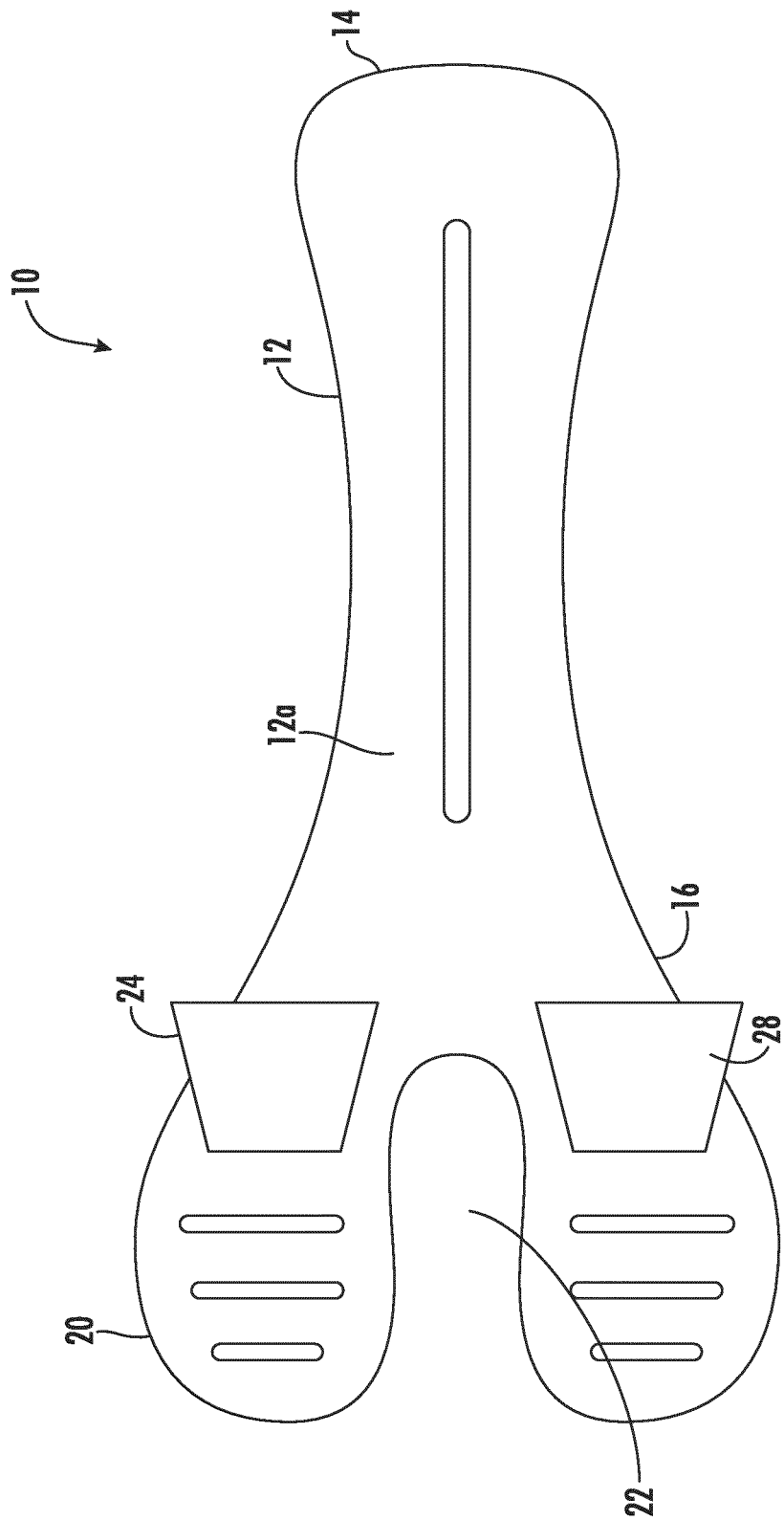
FIG. 2 is a top view of the joint gap balancing lever of FIG. 1, according to an exemplary embodiment.
Figure 3:
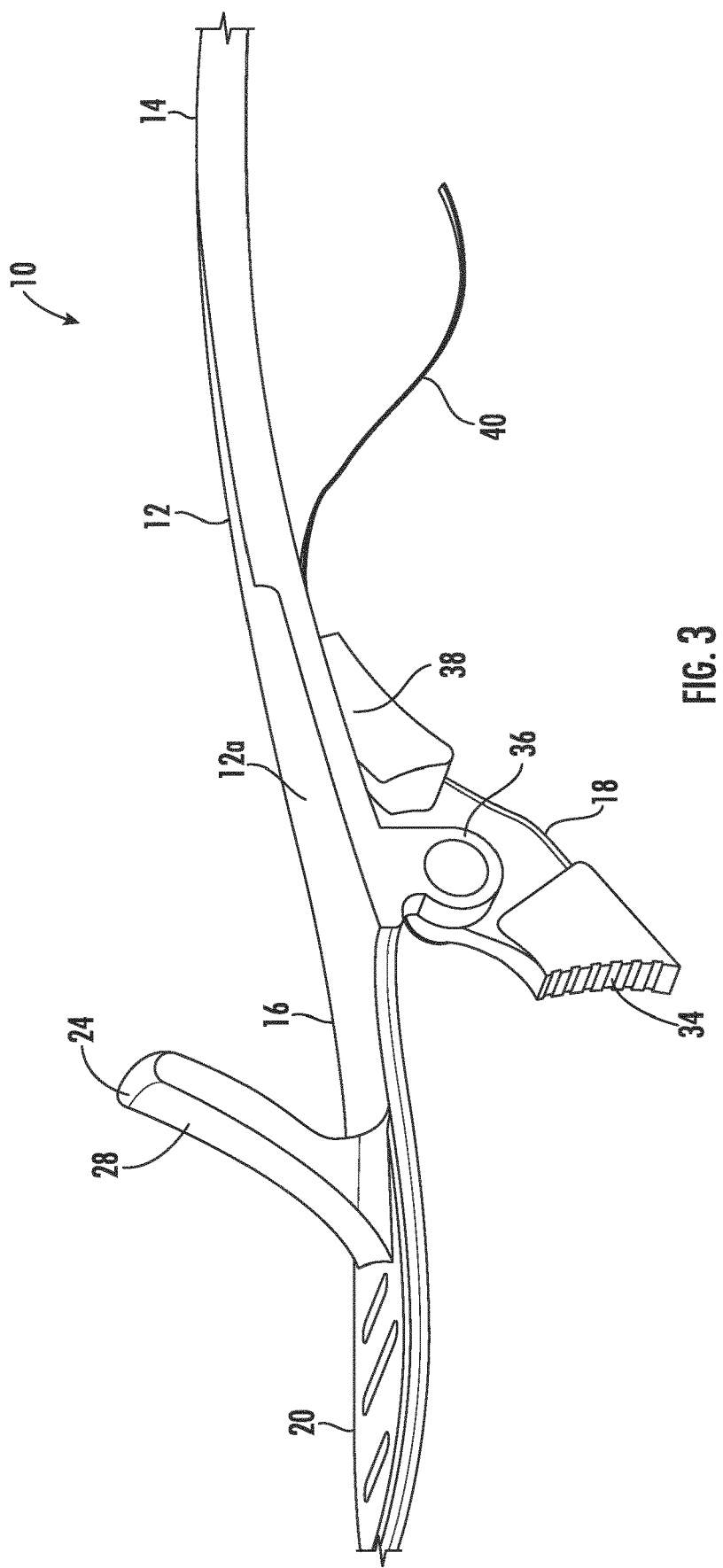
FIG. 3 is a lateral side cross-sectional view of the joint gap balancing lever of FIG. 1, taken along a lengthwise median line, according to an exemplary embodiment.

Referring to FIGS. 1-3, a joint distraction device is shown. In certain embodiments, the joint distraction device is a joint gap balancing lever device 10 (referred to herein as device 10). Though the present description will refer to the joint gap balancing lever as the device 10, it is to be understood that the features disclosed herein may be used with and provided in a variety of distraction lever-type and gap-balancing devices, which are considered to be within the scope of the present disclosure. As shown in FIGS. 1-3, the various embodiments of device 10 include a lever body 12, having a top surface 12a and a bottom surface 12b. The lever body includes a proximal portion 14 and a distal portion 16. A foot 18 extends from the bottom surface 12b of the lever body 12 at the distal portion 16. Also at the distal portion 16, the lever body 12 splits into two plates 20, which are separated by a gap 22. Extending upwards from the top surface 12a of each of the plates is a stopper 24. In some embodiments, the distal portion 16 including the plates 20 of the lever body 12 is slightly curved to accommodate the non-planar surface of the bone.

The device 10 has a thin, narrow lever body 12 sized to be inserted into a joint space. In various embodiments, the lever body 12 is between 1.0 mm and 4.0 mm thick at the distal portion 16 at plates 20. In certain embodiments, the lever body 12 is approximately 2.05 mm thick at the distal portion 16 at plates 20 and, in other embodiments, no more than approximately 3.50 mm thick. The width of the plates 20 is between 70.0 mm and 85.0 mm wide. In certain embodiments, the width of the plates 20 is approximately 81.0 mm wide to accommodate compartments of various sizes, and in a preferred embodiment, are approximately 74.0 mm wide.

The proximal portion 14 is configured to be gripped by a user during use of the device 10. In some embodiments, the proximal portion 14 is shaped like a handle, with a slight curve downward toward the distal end. Although the proximal portion 14 is static in the embodiment shown in FIGS. 1-3, in some embodiments, the joint gap balancing lever has a rotatable proximal portion 14. A rotatable proximal portion 14 allows for a reduction in the amount of torque working laterally during joint distraction. For example, when distracting the knee joint, the distraction force should be provided substantially parallel with the mechanical axis of the joint. However, the surgeon may not be able to achieve exact access and grip on the tool such that all forces are being applied in this direction. As a result, some torque may instead be applied sideways on the joint while also being applied in parallel with the mechanical axis. A rotatable proximal portion 14 may counteract some of the sideways torque applied by cooperating with the twisting that may occur on the handle when the force is applied at the proximal portion 14.

Figure 4:
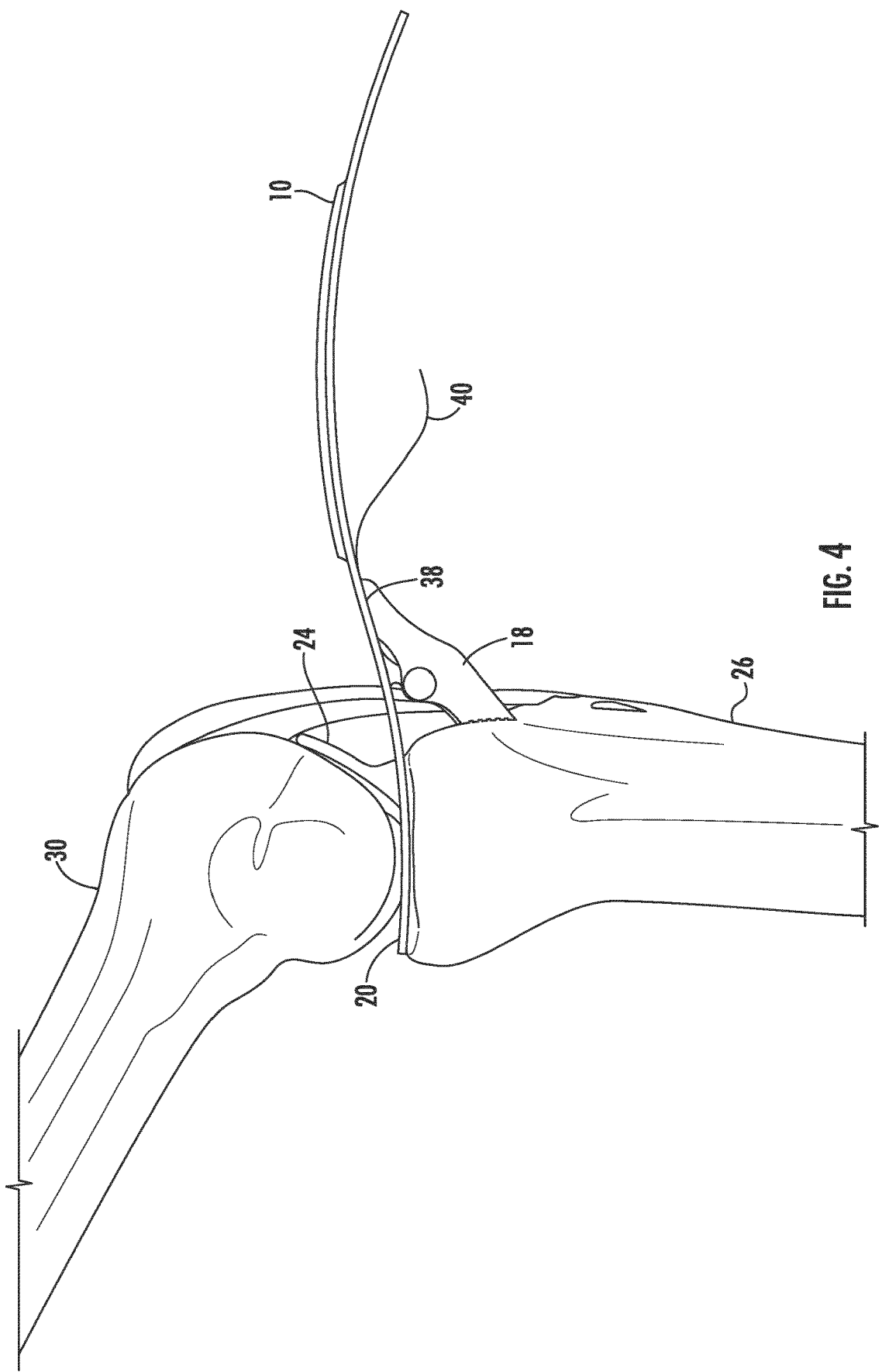
FIG. 4 is a side view of the joint gap balancing lever in use during a distraction procedure, according to an exemplary embodiment.
Figure 5:
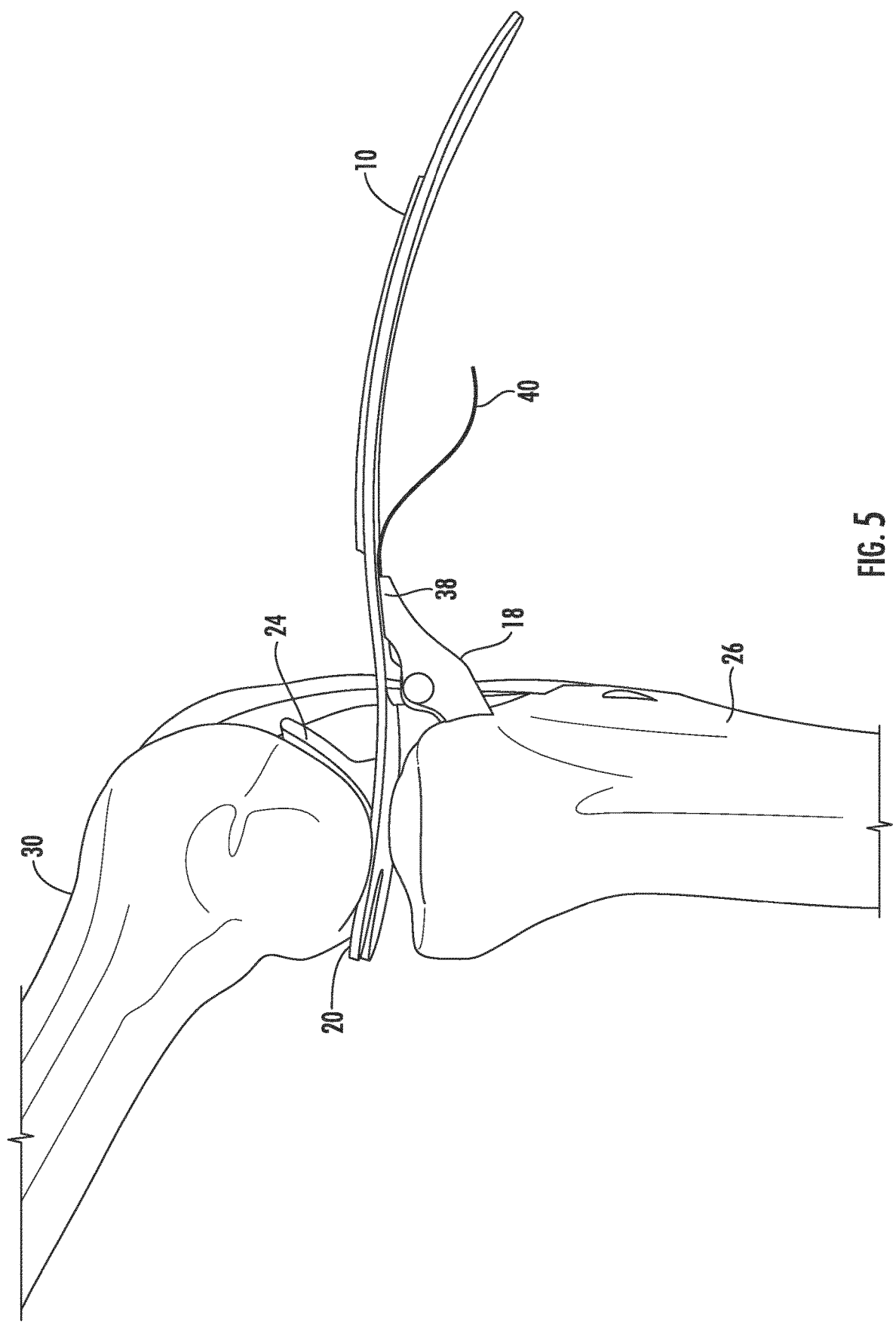
FIG. 5 is a side view of the joint gap balancing lever in use during a distraction procedure following distraction, according to an exemplary embodiment.

The distal portion 16 is configured to transmit a force provided by the user at the proximal portion 14 to a bone of a joint. Referring now to FIGS. 4-5, the device 10 is shown in use, according to an exemplary embodiment. As shown in FIGS. 4-5, the foot 18 of the device 10 is configured to rest on a first bone (e.g., a longitudinal surface of a patient's tibia 26) and apply a force to a second bone (e.g., a femoral condyle 32 of a patient's femur 30). However, it should be understood that while the embodiments of the joint gap balancing lever are depicted and described herein and being used in a knee joint, the joint gap balancing lever may be used in any joint that is suitable for a joint distraction procedure. Resting the foot 18 on the longitudinal surface (such as a front facing surface) of the tibia 26 provides support for the device 10 as a torque is applied at the proximal portion 14. The torque is then provided to the femur 30 through the plates 20 at the distal portion 16, which are inserted between the tibia 26 and femur 30. The provided torque causes distraction of the joint (e.g., separation of the first and second bones of the joint), which is shown in FIG. 5 as a separation of the tibia 26 and the femur 30.

Accordingly, the joint gap balancing lever according to various embodiments is dependent on the force applied to the bone at two known locations: the foot 18 and the plates 20. To ensure that forces are being applied only at these two locations, the foot 18 projects from the bottom surface 12b of the device, while the plates 20 and corresponding stoppers 24 project from the top surface of the device 10, such that the lever body 12 does not slide during the distraction procedure and contact is maintained between the bone and the plates 20.

Referring first to the foot 18, the foot 18 is designed to project from the bottom surface 12b of the lever body 12 to a distance sufficient to provide proper torque during use. As an example, the foot 18 is configured to press up against the longitudinal surface of the tibia 26 via a frontal face 34 of the foot 18. In the embodiment shown in FIG. 1, the foot 18 comprises two prongs, such that there are two frontal faces 34 of the foot 18. In other embodiments, the foot 18 comprises a single prong. The frontal face 34 of the foot 18 is configured to provide a greater surface in contact with the bone to minimization penetration into the bone, when such penetration would be detrimental or undesirable. As such, the frontal face 34 of the foot 18 is configured to abut a surface of the first bone, such that the frontal face 34 rests upon the surface of the first bone, rather than to penetrate into the first bone. The frontal face 34 of the foot 18 may include a plurality of grooves in order to prevent slipping and any other movement of the foot 18 relative to the first bone during a distraction procedure. In some embodiments, the foot 18 is coupled to the bottom surface 12b of lever body 12 via a hinge 36. The hinge 36 allows the lever body 12 to pivot or rotate during a distraction procedure, and may be used to measure the torque applied to the proximal portion 14. The lever body 12 is allowed to pivot via the hinge 36 relative to the foot 18 during a distraction procedure. Accordingly, the frontal face 34 of the foot 18 presses into the first bone, such as the longitudinal surface of a tibia 26, when the torque is applied to the proximal portion 14 of the lever body 12.

The joint gap balancing lever, such as device 10, is configured to measure and provide output related to the distraction force applied to the bone of the joint during a distraction procedure. The distraction force is measured by a force measurement device 40. In some embodiments, the force measurement device 40 is positioned between a back face 38 of the foot 18 and the bottom surface 12b of lever body 12, such that the force measurement device 40 measures the force provided between the lever body 12 pressing into the back face 38 of the foot 18 when a force is applied to the lever body 12 to distract the joint. In some embodiments, the distraction force measured by the force measurement device is evaluated to perform joint gap balancing. For example, the distance between the first and second bones can be measured throughout the distraction procedure as a function of the distraction force measured by the force measurement device. In some embodiments, an optimal gap distance between the first and second bone, as further discussed below, can be determined based on the feedback from the force measurement device. As an example, the optimal gap distance can be determined by the juncture at which the force continues to rise while the measured gap remains static.

In some embodiments, the force measurement device is a force gauge. One or more force gauges may be coupled at the foot 18 of the lever body 12 and configured to receive an input voltage provided by a power source. In certain embodiments, the power source is a battery. The battery may be disposable, rechargeable, or take the form of a chargeable capacitor. As the electrical conductor of the force gauge measures the rise in force, the distraction lever elevates the joint. When torque is applied to distract the bones of the joint, the electrical resistance of the electrical conductor of the force gauge changes. Thus, from the measured electrical resistance of the force gauge(s), computed using the known or measured input voltage and measured output voltage, the amount of applied stress to distract the joint can be measured and the distraction force computed. A plurality of force gauges may be arranged and included in the foot 18 to form a load cell. The output of the load cell transducer can then be used to convert the force or stress determined by the force gauges into an electrical signal.

Other mechanisms or tools for measuring the distraction force applied by the joint gap balancing lever at the foot 18 include piezoelectric pressure sensors wherein a charge is generated when a piezoelectric crystal, or other suitable material, of the pressure sensor is stressed. The charge output, or the charge output converted to a voltage signal, for example, may be used to compute and indicate the distraction force being applied by the distraction lever. Similarly, stress to the lever body 12 to compute the distraction force applied at the foot 18 can be determined using optical sensors in a cantilever beam configuration. The optical sensors may include an array of optical fibers capable of providing computation of stress and strain by way of wavelength variations between the light source and a detector caused by modifications in the optical fiber body. Finally, a magnetic contact switch may be used to indicate the presence of a load being applied, or can be configured to indicate how much load is being applied.

Referring back to FIGS. 1-3, the plates 20 extend from the distal portion 16 of the lever body 12. In the embodiments shown, there are two plates 20. In other embodiments, a single plate 20 extends from the distal portion 16 of the lever body 12. There is a gap 22 between the two plates 20. In the embodiment shown, the plates 20 form a relatively flat surface, and have a slightly rounded shape towards the most distal portion. In some embodiments, the plates 20 are slightly curved to fit with the outer surface of the bone. In some embodiments, the plates 20 are specifically configured for a particular bone or the anatomy of a particular patient. The configuration of the plates 20 provides greater contact surface area for torque transmission efficiency as well as to reduce penetration of the bone being distracted. In some embodiments, the surface of the plates 20 have a plurality of grooves or other indents that are configured to minimize movement of the bone relative to the plates 20. Other configurations of the plates 20 and the distal portion 16 are also used in accordance with additional embodiments of the present disclosure.

The plates 20 each comprise a stopper 24 extending vertically upwards from the top surface 12a of the plates 20 on the distal portion 16 of the lever body 12. In the embodiment shown, the stoppers 24 each have a frontal face 28. In some embodiments, the frontal face 28 is slightly concave. The frontal face 28 of the stoppers 24 is configured to abut a surface of the second bone, such as the femoral condyle 32 of the femur 30. In some embodiments, the stoppers 24 do not transmit a significant force to the second bone. Rather, the frontal face 28 of the stoppers 24 is configured to provide a resting spot for the second bone, and to prevent forward movement of the second bone during a distraction procedure or slippage of the device 10. In some embodiments, the frontal face 28 of the stoppers 24 have a plurality of grooves or other indents that are further configured to prevent movement of the second bone relative to the stoppers 24. The stoppers 24 of the plates 20 may further be configured to provide support and stability to the lever body 12 throughout the distraction procedure.

Figure 6:
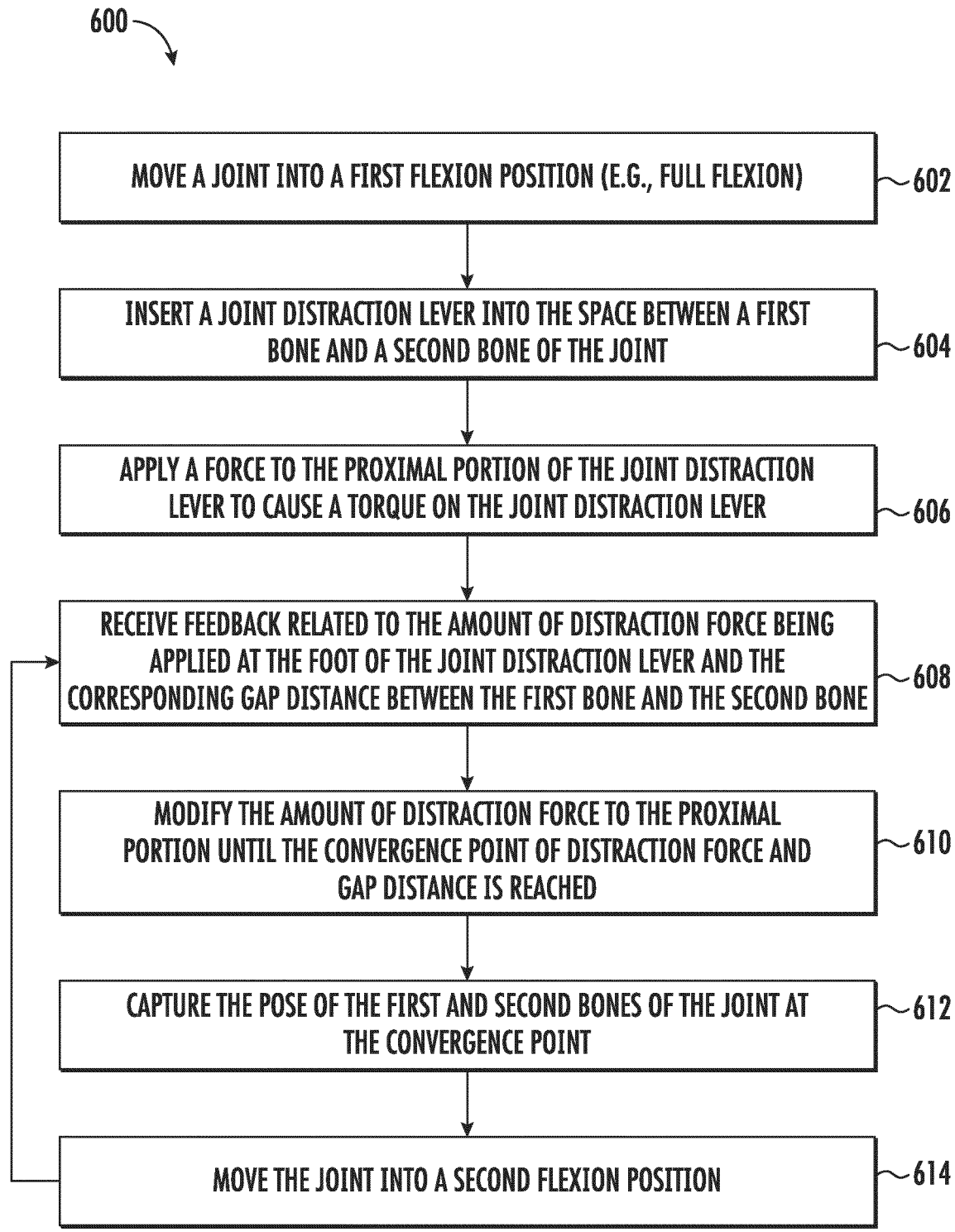
FIG. 6 is one embodiment of a method for performing joint distraction using a joint gap balancing lever, according to an exemplary embodiment.

Referring to FIG. 6, a method 600 for performing gap balancing using a joint gap balancing lever is depicted, according to an exemplary embodiment. In step 602, a joint, such as the knee joint including the tibia 26 and the femur 30, is first moved into a first flexion position. For example, the first flexion position is full flexion, though any range of flexion may be used.

Figure 9:
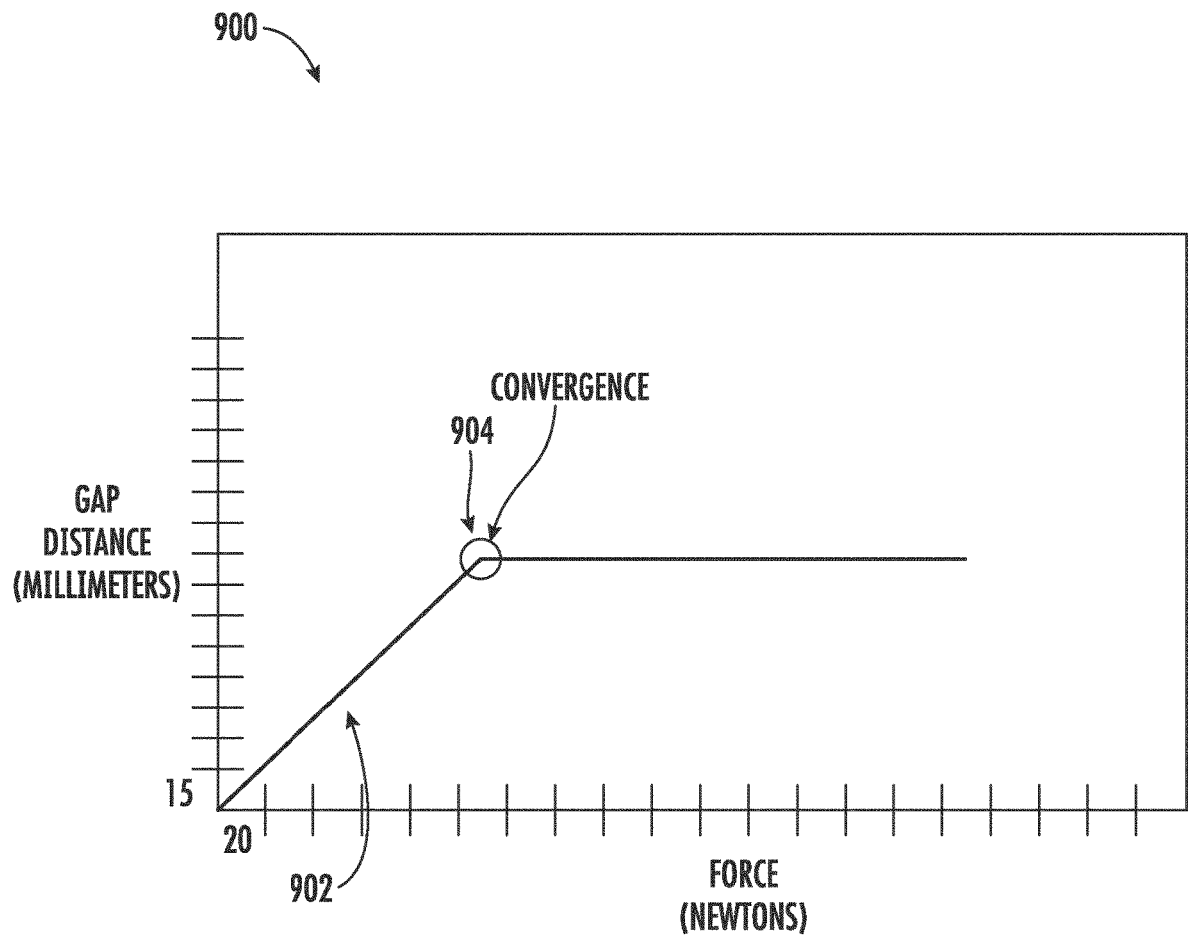
FIG. 9 is a graph depicting the convergence point of the gap distance versus the force applied by the joint gap balancing lever, according to an exemplary embodiment.

At step 604, a joint gap balancing lever, such as device 10 according to the exemplary embodiments disclosed herein, is inserted into the space between the first and second bones of the joint. An external force is then applied to the proximal portion 14 of the lever body 12 to cause a torque on the joint gap balancing lever (step 606). As a result, in step 608 the user receives feedback related to the amount of distraction force being applied to the first or the second bone of the joint at the foot 18 of the joint gap balancing lever, as measured by a force measurement device 40. Additionally, at step 608, the user receives feedback related to the corresponding gap distance between the first bone and the second bone of the joint, such as the tibia 26 and the femur 30. To measure the gap distance, the joint gap balancing lever may be used in conjunction with anatomy navigation systems and methods associated with a surgical system, such as those depicted in FIG. 7 and described below. At step 610, the user modifies, if necessary, the amount of distraction force applied to the proximal portion 14 of the lever body 12 in order to obtain an optimal gap distance between the first bone and the second bone of the joint for proper balancing of the soft tissue. In some embodiments, the optimal gap distance is correlated to amount of force applied to the proximal portion 14 of the lever body 12. For example, as seen in FIG. 9, there is a point of convergence between the gap distance and the force applied. In some embodiments, this point of convergence corresponds to the optimal gap distance.

At step 612, a pose of the first and second bones of the joint is captured at the optimal gap distance and using the corresponding force needed to achieve the optimal gap distance. Capturing the pose of the first bone and the second bones of the distracted and properly balanced joint assists with surgical planning to ultimately attain the desired, properly aligned joint post-resection and post-prosthetic implantation.

At step 614, the joint is optionally moved to a second flexion position and may further be moved to any number of additional flexion positions as needed. In moving the joint to a subsequent flexion position, the user again receives feedback related to the amount of distraction force being applied at the foot 18 of the joint distraction lever and the gap distance between the first and second bone until the optimal gap distance is achieved, and the pose of the bones captured.

In various arrangements, these poses of the flexion position(s), with the distraction force to achieve optimal gap distance applied, represent the desired post-resection final position of the joint (e.g., the knee joint). Accordingly, bone resection, implant positioning, and implant characteristics are planned (e.g., using the computing system 720 described below) using the poses captured during the gap balancing process (e.g., the method 600). Once the bone is resected at this desired plan and the trials and/or implants are secured to the bone, the leg will ideally experience the proper balance through the range of motion.

Figure 7:
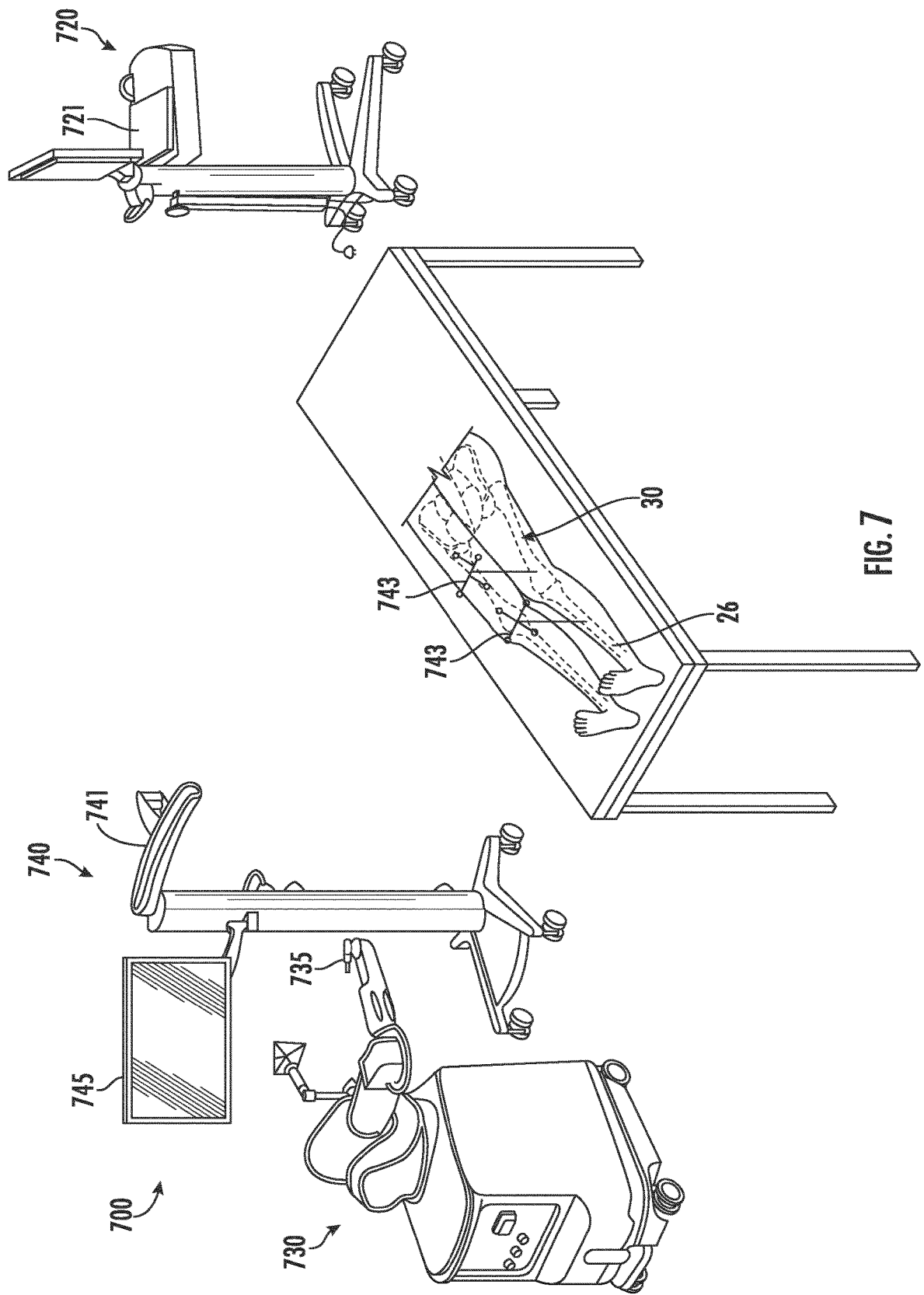
FIG. 7 is a surgical system with which a joint gap balancing lever may be used, according to an exemplary embodiment.

The surgical system 700 depicted in FIG. 7, used in conjunction with the joint gap balancing lever device 10, is used, for example, to capture the poses of the bones of the joint, as well as others aspects of surgical planning. FIG. 7 illustrates a surgical system 700 that includes a computing system 720, a surgical tool such as haptic device 730, and a tracking system 740. In operation, the surgical system 700 enables comprehensive surgical planning, which may include performing distraction of a joint using the device 10 described herein.

Determining the gap distance between the first and second bones in step 608 and determining the pose of the first and second bones in step 612 may make use of the tracking system 740. The tracking (or localizing) system 740 of the surgical system 700 is configured to determine a pose (i.e., position and orientation) of one or more objects during a surgical procedure to detect movement and capture poses of the object(s). For example, the tracking system 740 includes a detection device 741 that obtains a pose of an object with respect to a coordinate frame of reference of the detection device. As the object moves in the coordinate frame of reference, the detection device 741 tracks the pose of the object to detect (or enable the surgical system 700 to determine) movement of the object. Tracked objects include, for example, tools/instruments, patient anatomy, implants/prosthetic devices, and components of the surgical system 700. Using pose data from the tracking system 740, the surgical system 700 is also able to register, map, or associate coordinates in one space to those in another to achieve spatial alignment or correspondence (e.g., using a coordinate transformation process as is well known). Objects in physical space are registered to any suitable coordinate system, such as a coordinate system being used by a process running on the computer 721.

For example, utilizing pose data from the tracking system 740, the surgical system 700 is able to associate the physical anatomy with a representation of the anatomy (e.g., an image displayed on a display device 745). Based on tracked object and registration data, the surgical system 700 determines, for example, a spatial relationship between the image of the anatomy and the relevant anatomy. Additionally, by tracking the relevant anatomy, the surgical system 700 can compensate for and ascertain movement of the relevant anatomy during the surgical procedure, as needed for capturing the pose of the distracted joint at the flexion position.

Registration may include any known registration technique, such as, for example, image-to-image registration (e.g., monomodal registration where images of the same type or modality, such as fluoroscopic images or MR images, are registered and/or multimodal registration where images of different types or modalities, such as MM and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and Mill images to an intraoperative scene).

The tracking system 740 may also be used to track the anatomy and the device 10, while applying the distraction force. By tracking the pose (i.e., position and orientation) and the movement of the device 10 and the bones of the joint, such as tibia 26 and femur 30, the computing system 720 is able to determine the directional components of the force being produced. In addition to the forces acting along the mechanical axis of the bone being moved, the distraction force may also act in a lateral direction or other direction off-axis from the mechanical axis. Tracking of the objects used during a distraction procedure and determination of the directional components may allow for a determination of the amount of force that is off of the intended axis. This may help the surgeon adjust the application of force for more efficient load transmission and/or to reduce any injury or damage that may occur while applying distraction forces in directions that are off of the intended axis.

The tracking system 740 is any tracking system that enables the surgical system 700 to continually determine (or track) a pose of the relevant anatomy of the patient and a pose of the tool 735 (and/or the haptic device 730). For example, the tracking system 740 comprises a non-mechanical tracking system, a mechanical tracking system, or any combination of non-mechanical and mechanical tracking systems suitable for use in a surgical environment.

A mechanical tracking system relies on a physical connection between the detection device 741 and the tracked object. For example, a mechanical tracking system includes one or more mechanical arms that are coupled to the tracked object and to the detection device 741. The detection device 741 detects the position and orientation of the object based on the movement of the tracked object that is sensed by the mechanical arm(s).

A non-mechanical tracking system includes, for example, an optical (or visual), magnetic, radio, or acoustic tracking system. Such systems include a detection device adapted to locate in a predefined coordinate space specially recognizable trackable elements ("trackers") that are detectable by the detection device and that are either configured to be attached to the object to be tracked or are an inherent part of the object to be tracked. For example, a trackable element includes an array of markers having a unique geometric arrangement and, when attached to the tracked object (e.g., the femur 30 and tibia 26 of a patient), a known geometric relationship to the tracked object. These markers include any known marker, such as extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device 741. Intrinsic features are salient and accurately locatable portions of the tracked object that are sufficiently defined and identifiable to function as recognizable markers for the detection device 741 on their own (e.g., landmarks, outlines of anatomical structure, shapes, colors, or any other sufficiently recognizable visual indicator).

The markers may be located using any suitable detection method, such as, for example, optical, electromagnetic, radio, or acoustic methods as are well known. For example, an optical tracking system having a detection device 741 implemented as stationary stereo camera pair sensitive to infrared radiation may be used to track markers that emit infrared radiation either actively (e.g., as LEDs) or passively (e.g., spherical markers with surfaces that reflect infrared radiation). Similarly, a magnetic tracking system may include a stationary field generator that emits a spatially-varying magnetic field sensed by small coils integrated into the tracked object.

Figure 8:
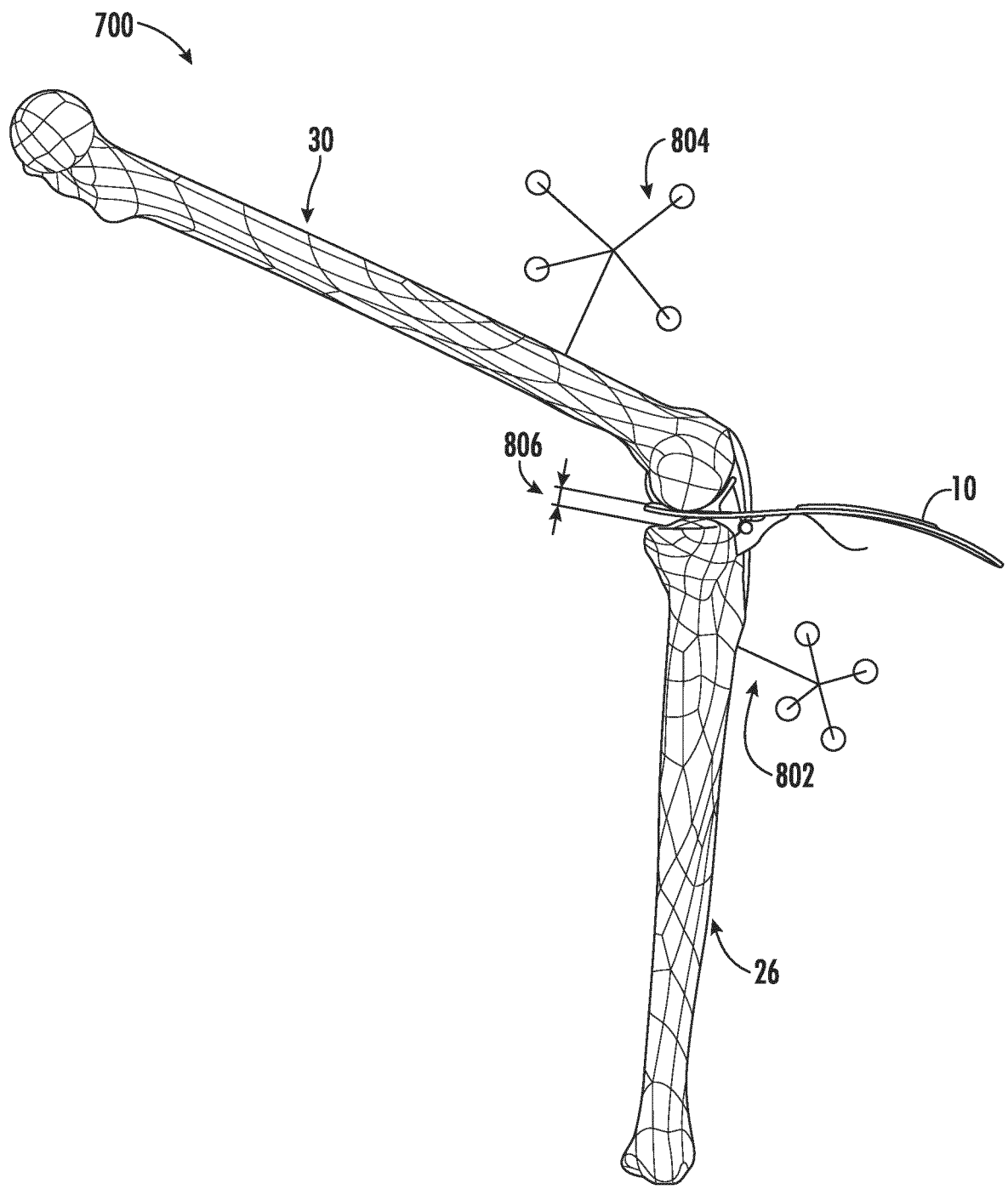
FIG. 8 is a side view of the joint gap balancing lever in use with the surgical system of FIG. 7, according to an exemplary embodiment.

In the embodiment shown in FIG. 7, the tracking system 740 includes a non-mechanical tracking system. In this embodiment, the non-mechanical tracking system is an optical tracking system that includes an optical detection device 741 and at least one tracker 743, such as anatomy trackers, configured to be disposed on, or incorporated into, a tracked object and detected by the detection device 741. The trackers 743 are configured to be affixed to the tracked object in a secure and stable manner (e.g., to the tibia 26 and the femur 30, as shown in FIG. 7), and each tracker 743 includes an array of markers having a known geometric relationship to the tracked object. In some embodiments, such as shown in FIG. 8, the tracking system 740 comprises both a tibia tracker 802 and a femur tracker 804. In some embodiments, the tibia tracker 802 and the femur tracker 804 are configured to track a gap distance 806 between the tibia 26 and femur 30 during a distraction procedure, as described further below. FIG. 8 is a side view of the joint gap balancing lever in use with the surgical system 700.

As described above, the markers may be active (e.g., LEDs) or passive (e.g., reflective spheres, a checkerboard pattern, etc.). In some arrangements, the markers have a unique geometry (e.g., a unique geometric arrangement of the markers) or, in the case of active, wired markers, a unique firing pattern. In operation, the detection device 741 detects the positions and orientations of the markers (e.g., including the unique geometry or firing pattern) and use a known geometric relationship to the tracked object enable the surgical system 700 to calculate a pose of the tracked object based on the positions of the markers.

As stated above, a virtual representation of the anatomy, such as the knee joint, can be displayed on display device 745. In some embodiments, the display device 745 also displays the distraction force measurement obtained by a force measurement device of the joint gap balancing lever. For example, as described above, the device 10 communicates wirelessly (e.g., Bluetooth, RFID, etc.) or via a coupled connection with the surgical system 700 to provide the distraction force measurement for display on an external device, such as the display device 745. Furthermore, as also described above, the device 10 may include a button in response to which the surgical system 700 captures the pose of the joint using the tracking system 740 (e.g., because pressing the button causes the device 10 to transmit a command to the surgical system 700 to capture the pose of the joint). The surgical system 700 may further display pose information on the display device 745 and/or use the pose information to complete a surgical planning procedure.

Accordingly, in various embodiments, the computing system 720 is configured to acquire and use the data obtained during a joint distraction procedure, including pose information (e.g., captured in response to the user pressing a button on the device 10), to complete a surgical planning procedure. Thus, computing system 720 may capture and store the pose of the first and second bones of the joint based on information captured and provided by tracking system 740. For example, the captured pose of the joint may be used to plan bone resection and prosthetic implant placement for proper joint balance and alignment. In some embodiments, the computing system 720 of surgical system 700 is further configured to define a surgical plan based on the captured pose(s) of the distracted joint. In some such embodiments, the surgical system 700 then implements the surgical plan, for example, by using the tracking system 740 to track the pose of a surgical tool relative to the patient's anatomy and providing haptic feedback through the haptic device 730 (e.g., based on a position and orientation of a surgical tool 735 relative a haptic boundary created during surgical planning). The haptic feedback provided by the haptic device 730 provides surgical guidance to a surgeon in order to keep the surgical tool 735 from deviating from the surgical plan created based on the joint distraction procedure and other aspects of surgical planning.

U.S. Pat. No. 8,010,180, titled "Haptic Guidance System and Method," granted Aug. 30, 2011, which is hereby incorporated by reference herein in its entirety, describes an exemplary surgical system with which the presently described joint gap balancing lever may be used during a joint distraction procedure and for bone resection and implant planning.

In some embodiments, surgical system 700 is configured to determine an optimal gap distance between the first and second bones of the joint, such as the tibia 26 and the femur 30. In some embodiments, the optimal gap distance corresponds to the maximum gap distance that can safely be achieved between the first and second bones. In some embodiments, the gap distance is determined by tibia tracker 802 and femur tracker 804, which are configured to determine the gap distance between the tibia 26 and the femur 30. In other embodiments, the optimal gap distance corresponds to the greatest gap distance that is obtained without exceeding a certain force limit. The force limit may be predetermined, or may be determined by a user based on the feedback from the force measurement devices used at the foot 18 of device 10. As described above, tracking system 740 is configured to provide the location of the bones of the joint during the distraction procedure, which can be captured and stored via the computing system 720. The display device 745 may be configured to display, in real time, the gap distance between the first and second bones throughout the distraction procedure along with the distraction force applied in order to achieve that gap distance. In some embodiments, the display device 745 provides an alert as to when the maximum gap distance has occurred.

Referring now to FIG. 9, an exemplary embodiment of a graph 900, which may be displayed by display device 745, is shown, where line 902 illustrates the gap distance as a function of the force applied. In the embodiment shown, the gap distance is measured in millimeters, and corresponds to the distance between the tibia 26 and the femur 30. In some embodiments, the gap distance is measured by tracking system 740. The force is measured in Newtons, and corresponds to the force measured by the force measurement device 40 at the foot 18 of device 10. As illustrated in the graph 900, the gap distance increases substantially or entirely linearly until the convergence point 904 is reached. In other words, the gap distance increases substantially uniformly with the force for a period of time, until the convergence point 904 is reached, after which the force continues to rise while the gap distance remains substantially stable. The convergence point 904 is dependent on a calibrated starting point for both the measured gap distance and the corresponding force. In some embodiments, the convergence point 904 is the point at which the maximum gap distance is achieved. In some embodiments, the maximum gap distance obtained at the convergence point 904 corresponds to the optimal gap distance as described above. Throughout the distraction procedure, the force at the convergence point 904 can be applied to the foot 18 of the device 10 in order to maintain the maximum gap distance without using excessive force. In some embodiments, the surgical system 700 alerts the user as to when the maximum gap distance has been achieved, which helps to prevent the user from applying unnecessary excessive force during distraction. In some embodiments, the force at the convergence point 904 is then be stored by the surgical system 700 for use in future surgical planning. In some embodiments, surgical system 700 is configured to provide an indication to a user, such as by display device 745, as to when the force needed to achieve the maximum gap distance has been reached.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several The invention includes methods that may be performed using the subject devices. The methods may include the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

What is claimed is:

1. A joint distraction lever, comprising:
   a lever body;
   a projection coupled to the lever body such that the projection is movable relative to the lever body; and
   a force sensor positioned between the lever body and the projection and configured to measure a force of the projection on the lever body.

2. The joint distraction lever of claim 1, wherein:
   the projection comprises a first face and a second face;
   the first face is arranged to contact a first bone of a joint; and
   the force is provided between the second face and the lever body.

3. The joint distraction lever of claim 2, comprising a hinge coupled to the lever body and the projection, the hinge positioned between the first face and the second face.

4. The joint distraction lever of claim 2, wherein the lever body comprises a plate arranged to contact a second bone of the joint while the first face contacts the first bone of the joint.

5. The joint distraction lever of claim 1, wherein the lever body comprises a plate, wherein the projection is configured to contact a tibia while the plate contacts a femur when the joint distraction lever is used to distract a knee joint.

6. The joint distraction lever of claim 5, comprising a stopper projecting upwards from a top surface of the lever body and configured to contact the femur.

7. The joint distraction lever of claim 1, further comprising a stopper projecting upwards from a top surface of the lever body and having a concave frontal face.

8. The joint distraction lever of claim 1, wherein the force sensor comprises a load cell transducer.

9. The joint distraction lever of claim 1, wherein the force sensor comprises a piezoelectric load cell.

10. The joint distraction lever of claim 1, wherein the lever body splits, at a distal end of the lever body, into a first plate and a second plate separated by a gap.

11. A surgical system, comprising:
    a joint distraction lever, comprising:
       a lever body;
       a projection coupled to the lever body such that the projection is movable relative to the lever body; and
       a force sensor positioned between the lever body and the projection and configured to measure a force of the projection on the lever body; and
    a computing system communicable with the force sensor to acquire measurements of the force from the force sensor.

12. The surgical system of claim 11, further comprising a tracking system configured to provide, to the computing system, position information for bones of a joint while the joint distraction lever is used to distract the joint.

13. The surgical system of claim 12, wherein the computing system is programmed to associate the measurements of the force with gap distances determined based on the position information.

14. The surgical system of claim 13, further comprising a display screen, wherein the computing system is programmed to cause the display screen to display a real-time gap distance and a real-time force measurement.

15. The surgical system of claim 13, wherein the computing system is programmed to provide an indication to a user when an amount of the force needed to achieve a maximum gap distance is reached.

16. The surgical system of claim 13, wherein the computing system is programmed to identify a point of convergence between the gap distances and the measurements of the force.

17. The surgical system of claim 11, wherein:
the projection comprises a first face and a second face;
the first face is arranged to contact a first bone of a joint; and
the force is provided between the second face and the lever body.

18. The surgical system of claim 17, comprising a hinge coupled to the lever body and the projection, the hinge positioned between the first face and the second face.

19. The surgical system of claim 17, comprising a stopper projecting upwards from a top surface of the lever body and positioned along the lever body between a distal end of the lever body and a hinge.

20. The surgical system of claim 11, wherein the lever body comprises a plate, wherein the projection is configured to contact a tibia while the plate contacts a femur when the joint distraction lever is used to distract a knee joint.

\* \* \* \* \*